United States Patent [19]

Baker et al.

[11] Patent Number: 5,531,702

[45] Date of Patent: Jul. 2, 1996

[54] PATIENT CONTROLLED SELF INJECTION AID

[75] Inventors: Denise J. Baker; Glenn D. Blankenhorn, III; Lonnie R. Freeman, all of Massillon; Heather B. Hann, Navarre; Judy A. Hesse, North Canton; Judy M. Kaforey, Akron; Darlene K. Piero, Canton, all of Ohio

[73] Assignee: Massillon Community Hospital, Massillon, Ohio

[21] Appl. No.: 434,577

[22] Filed: May 4, 1995

[51] Int. Cl.⁶ ........................................ A61M 5/00
[52] U.S. Cl. .............................. 604/181; 211/13
[58] Field of Search ..................... 604/181; 211/13, 211/60.1

[56] References Cited

U.S. PATENT DOCUMENTS

| | | |
|---|---|---|
| D. 312,870 | 12/1990 | Young. |
| 3,063,449 | 11/1962 | Schultz. |
| 4,338,935 | 7/1982 | Wilson. |
| 4,471,765 | 9/1984 | Strauss et al.. |
| 4,638,799 | 1/1987 | Moore. |
| 4,737,151 | 4/1988 | Clement et al.. |
| 5,232,448 | 8/1993 | Zdeb. |

Primary Examiner—Randall L. Green
Assistant Examiner—Perry E. Van Over
Attorney, Agent, or Firm—Donald R. Fraser

[57] ABSTRACT

A patient controlled self injection aid is provided to enable a user with one hand to draw medication from a reservoir into a syringe, self inject, and properly dispose of the needle and syringe.

6 Claims, 1 Drawing Sheet

U.S. Patent
Jul. 2, 1996
5,531,702
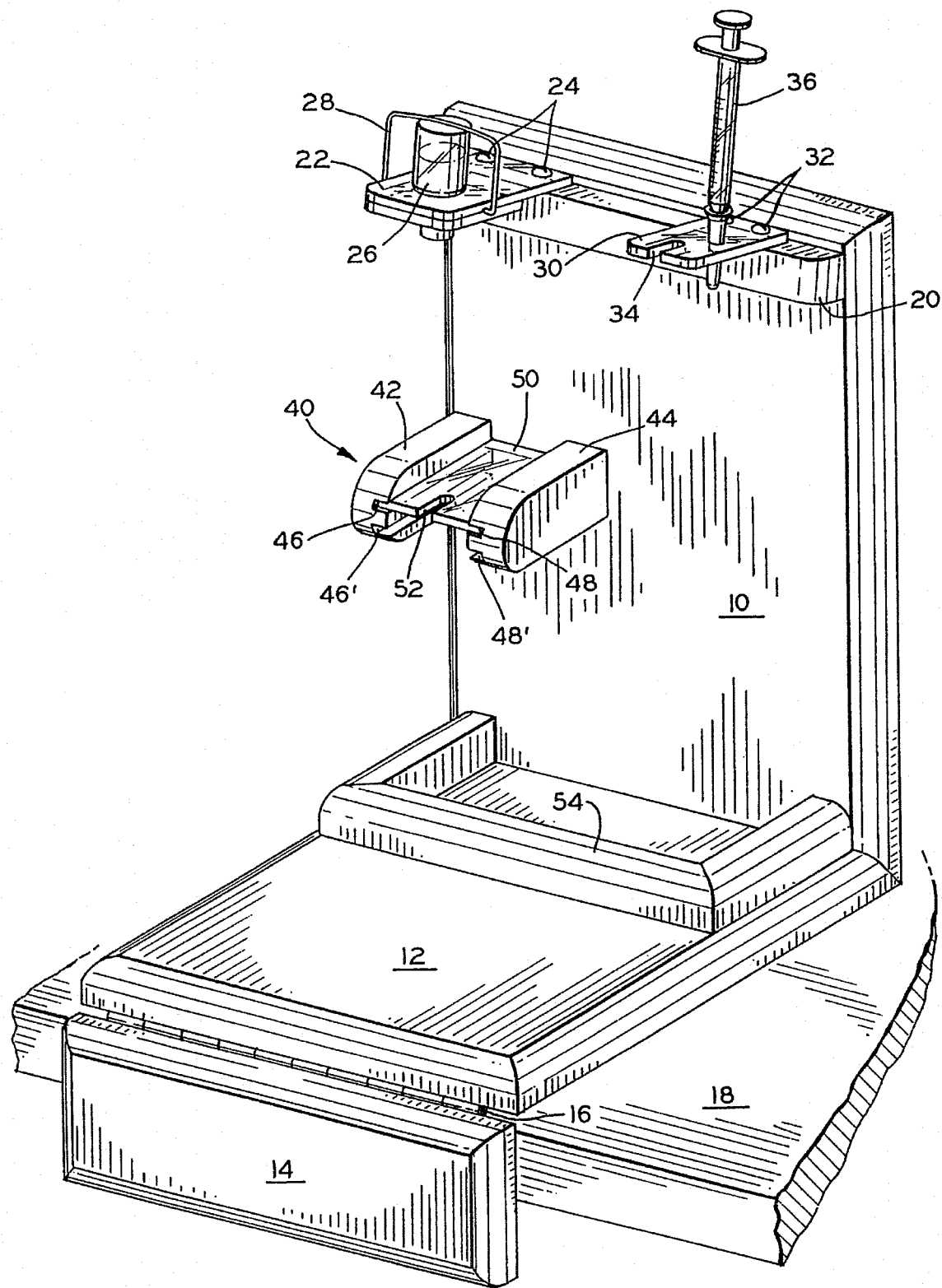

PATIENT CONTROLLED SELF INJECTION AID

FIELD OF THE INVENTION

The invention relates to a patient controlled self injection aid to enable the self injection of a medicament enabling the one handed self injection of the medicament.

BACKGROUND OF THE INVENTION

Many of the known patient controlled self injection aid systems have certain use limitations. These limitations include the fact that the aids have been relatively complex in structure and design and difficult to use. None of these structures provides a patient controlled aid which adequately enables a patient to easily to administer an injection of a medicament with a single hand.

It is an object of the present invention to produce a patient controlled self injection aid to enable a patient to self-administer a medicament with one hand.

Another object of the invention is to produce a patient controlled aid which will hold the medicament container and simultaneously hold the syringe needle cover to enable a patient to withdraw the syringe needle from its protective cover, insert the exposed needle into the medicament container, and fill the syringe with the predetermined dosage preliminary to self injection.

Another object of the invention is to produce a patient controlled aid which enables the removal of the syringe needle cover, the removal of a desired volume of a medicament from a reservoir, and facilitates "self injection" with a single hand.

SUMMARY OF THE INVENTION

The above objects of the invention may typically be achieved by a patient controlled self injection aid for disposition on a supporting surface for facilitating the removal of a protective cap from the needle portion of a syringe, the filling of a dose of medicament from a reservoir, and the subsequent single handed manipulation of the medicament containing syringe to perform a self injection, the improvement comprising: a main frame including a first upstanding member and a cooperating second member for maintaining the first member in a predetermined relative position; a medicament container holder mounted on the first member of the frame - a first syringe holder plate mounted on the first member of the frame, the plate including a syringe receiving aperture and a slot for engaging the protective cap from the needle of the syringe; a second syringe holder plate mounted on the first upstanding member of the frame beneath and in spaced alignment with the predicament container holder to hold the syringe during the filling thereof with the medicament from the container in the container holder - and means for militating against movement of the frame relative to the supporting surface.

Further objects and advantages of this invention will be apparent from the following description and appended claims, reference being made to the accompanying drawings forming a part of the specification, wherein like reference characters designate corresponding parts in the several views.

BRIEF DESCRIPTION OF THE DRAWINGS

The above, as well as the other objects and advantages of the invention, will become readily manifest to those skilled in the art from reading the following detailed description an embodiment of the invention when considered in the light of the accompanying drawings, in which:

FIG. 1 is a perspective view of the preferred embodiment of the invention.

DETAILED DESCRIPTION OF THE PREFERRED EMBODIMENT OF THE INVENTION

Referring to the drawings, there is illustrated a patient controlled self injection aid. More specifically, the aid includes a main frame comprised of an upstanding member 10 and an associated horizontally disposed member 12. An auxiliary member 14 is hingedly connected to the free end of the member 12 by a hinge 16. The main frame is typically disposed for use on a supporting surface 18 such as a counter top or a table top, for example. In an embodiment of the invention, it has been found that satisfactory results may be achieved by forming the members 10, 12, and 14 of the main frame of wood. The mating surfaces of the members 10 and 12 are mitered and then fastened to one another by suitable means such as glue and threaded fasteners.

A mounting rail 20 is secured to the upper marginal edge of the upstanding member 10. The rail 20 may be formed of wood and secured to the facing surface of the member 10. The rail 20 may be formed of wood and secured to the facing surface of the member 10 in any suitable manner such as by glue and/or threaded fasteners.

A medicament bottle holder 22 is secured to the rail 20 by threaded fasteners 24. The holder 22 may be formed of an optically transparent material such as an acrylic. The holder 22 is provided with an aperture of a diameter suitable to receive and hold the neck and shoulder portion of a medicament container 26. The cap of the container 26 depends downwardly from the under surface of the holder 22. A generally U-shaped clamp 28 is pivotally coupled to the holder 22. The clamp 28 is typically formed of a metal rod stock which is capable of being slightly springly deformed to pivot over the bottom of the container 26 to hold the same securely in the aperture of the holder 22. In order to remove the container 26 from the holder 22, the clamp 28 may be grasped and pivoted over the bottom of the container 26.

A syringe needle cap remover plate 30 is secured to extend outwardly from the rail 20 by threaded fastener 32. The plate 30 is provided with a slot 34 which is found to open at the outermost end of the plate 30. The plate 30 is additionally provided with an aperture suitable to receive and retain the protective cap portion of syringe 36.

A syringe plunger holding device 40 mounted on the facing surface of the upstanding member 10 in aligned position beneath the bottle holder 22. The plunger holding device 40 is comprised of two outwardly extending spaced apart supporting arms 42 and 44. The facing surfaces of the arms 42 and 44 are provided with horizontally disposed spaced apart facing slots 46, 46' and 48, 48', respectively. The uppermost slots 46 and 48, and the lowermost slots 46' and 48' cooperate to selectively slidingly receive a plate 50 having a slot 52 which is formed to open at the outermost end thereof. It has been found that satisfactory results may be typically achieved by forming the arms 42, 44 of wood and the plate 50 of a plastic material the same as that used to fabricate the holder 22 and the plate 30. The arms 42, 44 may be glued and/or screwed to the facing surface of the upstanding member 10 so that the associated plate 50 may function to adequately retain the syringe 36 during the filling thereof with medicament from the bottle 26 as will be discussed hereinafter.

An upstanding rail member 54 is secured to the facing surface of the horizontally disposed member 12 to define a zone to catch and maintain used syringe needle protective cups.

While mention has been made that the members 10 and 12 and the rails 20 and 54 may be fabricated from wood, it will be understood that other rigid materials may be satisfactorily employed. However, since the complete product is intended for medical use, the materials used in the construction thereof must be capable of being readily cleaned and maintained in a sterile condition.

In operation, the main frame is initially positioned on a supporting surface 18 such that the undersurface of the horizontally disposed member 12 is caused to rest on the facing support surface 18. The position of the horizontal member 12 may be maintained by the application of non-skid pads (now shown) and/or positioning the auxiliary member 14 along the outer marginal edge of the supporting surface 18, as illustrated in the drawing.

The medicament container 26 is then placed in the holder 22 by guiding the neck portion into and through the aperture found therein. At this stage, the shoulder of the container 26 rests against the peripheral marginal edge of the aperture of the holder 22. The container 26 is secured in the holder 22 by pivoting and springing the clamp 28 over the upstanding bottom of the container as illustrated in the drawings.

A sterilizing agent, such as alcohol for example, is typically employed to cleanse the stopper of the container 6. Then, the syringe 36 which had previously been placed in the aperture in the plate 30, is removed therefrom and the upper portion of the protective cap thereof is placed in the slot 34 of the plate 32. The main body of the syringe 36 is pulled downwardly to effectively remove the cap, thus exposing the needle portion of the syringe.

The needle of the syringe 36 is then caused to penetrate the stopper of the medicament container 26 to cause the open end of the needle to enter the medicament contained within the container.

The syringe 36 is swung toward the syringe plunger holding device 40 such that the syringe 36 is positioned within the slot 52 of the plate 50. The body of the syringe 36 is adjusted to permit the user to readily observe the volume denoting graduation lines and numbers. The plunger of the syringe 36 is pulled downwardly to the indicia indicating the predetermined dose of medicament. By the downward travel of the plunger, a vacuum is created within the interior of the syringe which, in turn, causes the medicament within the container 26 to flow into the syringe 36.

It must be understood that should the level of the medicament within the container 26 be low, the plate 50 of the syringe plunger holding device 40 may be guided out of the slots 46 and 48 and repositioned within the slots 46' and 48' to thereby extend the distance between the medicament containing bottle 26 and the syringe 36, thereby allowing the end of the syringe needle to be immersed in the medicament within the container 26.

The above procedure is followed by the normal cleansing of the skin of the user to be injected. After the skin has been cleansed, the syringe 36 is gently swung forwardly out of the slot 52 of the plate 50 and thence is moved downwardly to effectively remove the needle of the syringe 36 from the container 26.

With the single hand of the user, the needle of the syringe 36 is urged into the cleansed area of the user's skin and the medicament is injected by compressing the plunger of the syringe causing the predetermined medicament dosage to be administered.

Upon completion of the injection, the needle of the syringe 36 is inserted into protective cap resting in aperture of the plate 30. The syringe 36, including the used needle and associated protective cap, is disposed of in a proper receptacle. And, finally, the medicament bottle 26 is removed from the holder 22 by swinging the U-shaped clamp 28 about its pivots and releasing the container 26. The container 28 is returned to storage completing the entire use cycle of the injection aid structure of the invention.

It will be appreciated from the reading of the foregoing description the ease with which a patient required to use insulin, for example, may self inject the medicament with the use of the described aid. The invention enables users to be independent and provides them the ability to give their own medication rather than being dependent on another person to administer the medication.

In accordance with the provisions of the patent statutes, the present invention has been described in what is considered to represent its preferred embodiment. However, it should be understood that the invention can be practiced otherwise than as specifically illustrated and described without departing from its spirit or scope.

What is claimed is:

1. A patient controlled self injection aid for disposition on a supporting surface for facilitating the removal of a protective cap from the needle portion of a syringe, the filling of a dose of medicament from a reservoir, and the single handed manipulation of the medicament containing syringe to perform a self injection, the improvement comprising:

a main frame including a first upstanding member and a cooperating second member connected thereto for maintaining the first member in a predetermined relative position;

a medicament container holder mounted on the first member of said frame;

a first syringe holder plate mounted on the first member of said frame, said plate including a syringe receiving aperture and a slot for engaging the protective cap of the needle of the syringe;

a second syringe holder plate mounted on the first upstanding member of said frame beneath and in spaced alignment with said medicament container holder to hold the syringe during the filling thereof with medicament from the container in said container holder; and means for militating against movement of said frame relative to the supporting surface.

2. A patient controlled self injection aid as defined in claim 1 including spaced apart supporting arms for supporting said second syringe holder plate.

3. A patient controlled self injection aid as defined in claim 2 wherein said arms are provided with horizontally disposed slots for receivingly supporting said second syringe holder plate.

4. A patient controlled self injection aid as defined in claim 1 wherein said medicament container holder includes a pivotally mounted spring clamp for retaining the container.

5. A patient controlled self injection aid as defined in claim 1 wherein said means for militating against movement of said frame includes a third member pivotally affixed to the second member at a point spaced from the connection between the first member and the second member.

6. A patient controlled self injection aid as defined in claim 1 wherein said medicament container holder includes an aperture and an associated pivotally mounted spring clamp for retaining a container within the aperture.

* * * * *